United States Patent [19]
Liao et al.

[11] Patent Number: 5,480,526
[45] Date of Patent: Jan. 2, 1996

[54] METHODS FOR THE DESALTING OF BIOLOGICAL SAMPLES: A SIMPLE APPROACH TO ELIMINATE DISTURBANCES IN ISOELECTRIC FOCUSING CAUSED BY THE PRESENCE OF SALTS

[75] Inventors: Jia-li Liao; Rong Zhang, both of Upsala, Sweden; Christopher Siebert, Berkeley, Calif.

[73] Assignee: Bio-Rad Laboratories, Inc., Hercules, Calif.

[21] Appl. No.: 255,171

[22] Filed: Jun. 7, 1994

[51] Int. Cl.$^6$ .................................................. G01N 27/00
[52] U.S. Cl. .................. 204/182.8; 204/182.9; 204/183.2
[58] Field of Search ................ 204/182.8, 182.9, 204/183.2

[56] References Cited

U.S. PATENT DOCUMENTS

| | | | |
|---|---|---|---|
| 4,680,201 | 7/1987 | Hjerten | 427/230 |
| 4,971,670 | 11/1990 | Faupel et al. | 204/182.8 |

*Primary Examiner*—John Niebling
*Assistant Examiner*—Arun S. Phasge
*Attorney, Agent, or Firm*—Townsend and Townsend and Crew

[57] ABSTRACT

The present invention provides new methods for desalting samples of ionic polymers or weak electrolytes, preferable ampholytes (e.g., peptides, proteins and glycoconjugates) or, compounds which can be transformed into these substances by complex formation. The methods of the present invention are based on the fact that salts can be removed from a sample by electrophoretically replacing the salts with ampholytes present in the ampholytic media of the anolyte and the catholyte or, with displacing cations and anions that have been introduced into the anolyte and catholyte, respectively, and which have mobilities less than the mobilities of the cations and anions to be removed from the sample.

Although applicable to both small-volume and large-volume samples, the methods are particularly well suited for small-volume samples. Moreover, when applied to capillary electrophoresis, the methods described herein permit desalting of a sample in the same capillary tube as is used for the electrophoretic analysis. Alternatively, however, the sample can be withdrawn from the capillary tube following desalting and processed by techniques other than high-performance capillary electrophoresis (HPCE). Regardless of which method is used, the desalting methods of the present invention are rapid, highly reproducible, and they give a high recovery of sample compared to dialysis.

20 Claims, 3 Drawing Sheets

FIG. IE.
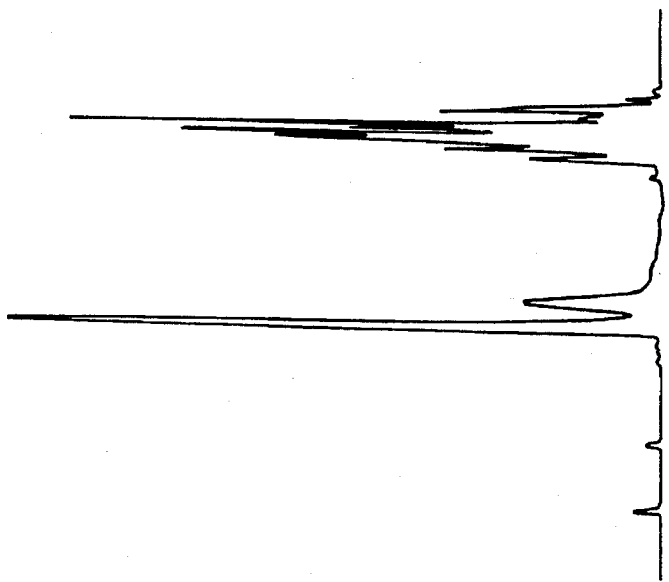
FIG. ID.

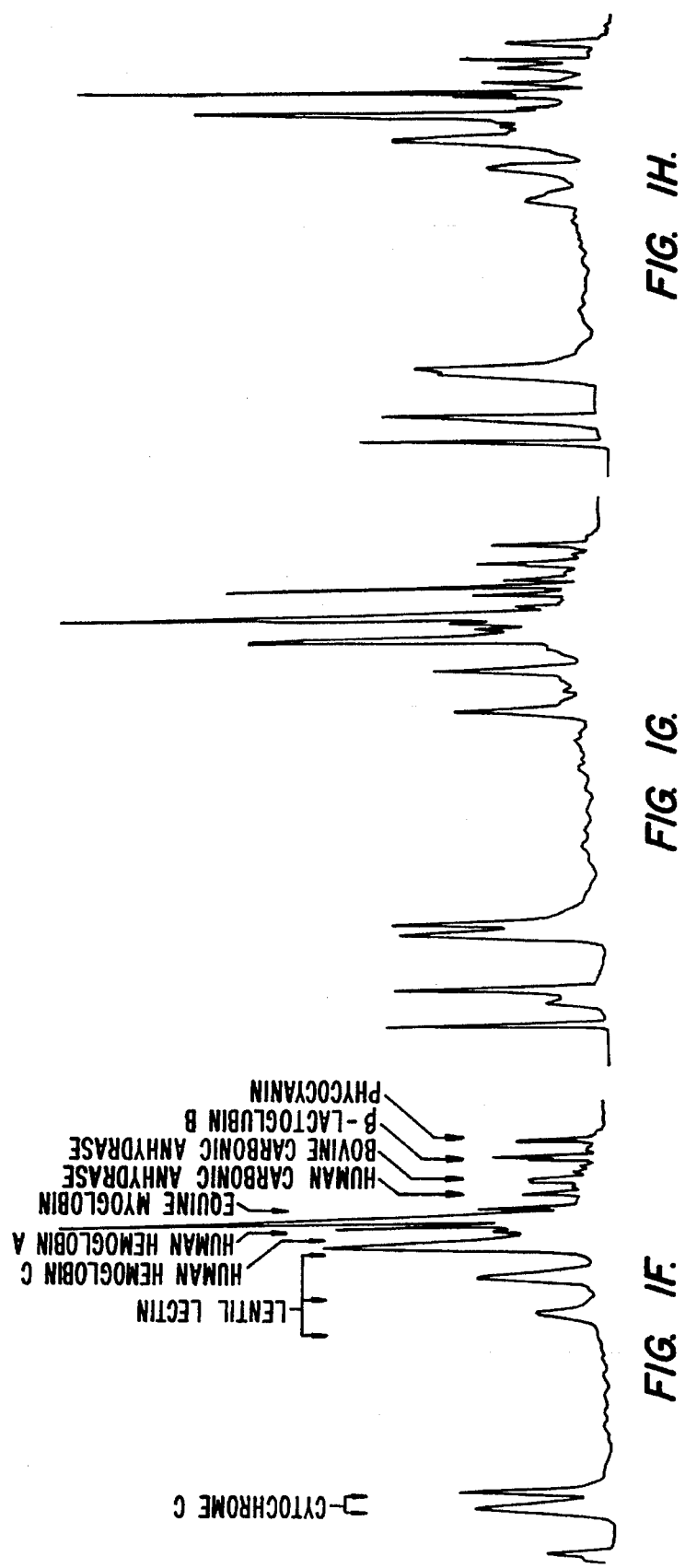

METHODS FOR THE DESALTING OF BIOLOGICAL SAMPLES: A SIMPLE APPROACH TO ELIMINATE DISTURBANCES IN ISOELECTRIC FOCUSING CAUSED BY THE PRESENCE OF SALTS

FIELD OF THE INVENTION

This invention lies in the field of capillary electrophoresis and relates, in particular, to methods for the desalting of biological samples including, for example, peptides, proteins, nucleic acids, glycoconjugates or mixtures thereof. Following desalting, the biological samples can be analyzed by high performance capillary electrophoresis or, by other techniques known to those skilled in the art.

BACKGROUND OF THE INVENTION

Capillary electrophoresis (CE) is a technique of considerable interest in the analysis of biological mixtures as it provides a number of distinct advantages over other separation processes. One advantage of capillary electrophoresis is the small volume of the capillary tube interior. This permits one to perform separations on extremely small volumes, i.e., on volumes ranging anywhere from a few nanoliters of sample to the cytosolic fluid of a single cell (T. M. Olefirowicz and A. G. Ewing, Anal. Chem., 62:1872–1876 (1990)). Another advantage of capillary electrophoresis is the rapid rate at which heat is dissipated outward from the capillary tube due to the capillary's narrow bore. This permits the use of a high voltage to drive the electrophoresis which, in turn, provides for separations at high speed and with high efficiency and resolution. Each of these advantages renders capillary electrophoresis particularly useful for analyzing samples of biological interest, particularly mixtures of peptides, proteins, and nucleic acids.

Moreover, capillary isoelectric focusing (CE-IEF) is a rapid and high resolution separation technique which can resolve proteins based on small differences in isoelectric points. CE-IEF has been applied to the separation of hemoglobins (S. Hjertén and M. Zhu, J. Chromatogr., 346:265–270 (1985)), transferrins (F. Kilár and S. Hjertén, Electrophoresis, 10:23–29 (1989)), and immunoglobulins (Wehr, et al., Am. Biotech. Lab., 8:22–29 (1990)). Although useful, an obvious disadvantage with all methods based on IEF is that many proteins precipitate at their isoelectric points, particularly at high protein and salt concentrations, and at elevated temperatures. More particularly, it is known that the presence of salt in a sample changes the pH gradient and confines the protein zone into a small segment of the capillary. This narrow pH gradient results in high protein concentrations and, in turn, in an increased risk of precipitation, loss of resolution and long mobilization times (Zhu, et al., J. Chromatogr., 559:479–488 (1991)). In addition, this narrow pH gradient contributes to localized overheating and, thus, to irreproducibility.

For the foregoing reasons, desalting of biological samples prior to capillary electrophoresis and, in particular, capillary isoelectric focusing is highly recommended. Unfortunately, the currently used desalting techniques frequently result in large sample losses when the sample volume is below 5 µl. To date, no desalting methods are available for sample volumes in the nanoliter range. As such, there still remains a need in the art for methods for the microscale desalting of biological samples. The present invention satisfies this need by providing such methods.

SUMMARY OF THE INVENTION

New methods have now been developed for the desalting of samples of ionic polymers or weak electrolytes, preferable ampholytes (e.g., peptides, proteins and glycoconjugates) or, compounds which can be transformed into these substances by complex formation. The methods of the present invention are based on the fact that salts can be removed from a sample by electrophoretically replacing the salts with ampholytes present in the ampholytic media of the anolyte and the catholyte or, with displacing cations and anions that have been introduced into the anolyte and catholyte, respectively, and which have mobilities less than the mobilities of the cations and anions to be removed from the sample.

In one aspect of the present invention, the sample to be desalted is mixed with an ampholytic separation medium to form a mixture, the ampholytic separation medium containing components capable of forming a pH gradient during isoelectric focusing, the pH gradient covering the isoelectric point(s) of the solute(s) present in the solute sample. A capillary tube then is filled with this mixture, the capillary tube having a first end in contact with an anolyte and a second end in contact with a catholyte, the anolyte and the catholyte being ampholytic media, the anolyte differing in pH from the catholyte by a pH differential. Subsequently, a voltage is applied between the anolyte and the catholyte of sufficient intensity to cause the salt present in the solute sample to be replaced by the ampholytes present in the ampholytic media of the anolyte and the catholyte.

In another aspect of the present invention, a method is provided for the desalting of a sample in an ampholytic separation medium having a first end in contact with an anolyte and a second end in contact with a catholyte differing in pH from the anolyte by a pH differential. In accordance with this method, the cations and anions of interest are removed from the sample by introducing a displacing cation into the anolyte and a displacing anion is introduced into the catholyte, the displacing cation having a mobility less than the mobility of the cation to be removed from the sample, the displacing anion having a mobility less than the mobility of the anion to be removed from the sample. Subsequently, a voltage is applied between the anolyte and the catholyte of sufficient intensity to cause the cation and the anion to be removed from the sample to be replaced by the displacing cation present in the anolyte and the displacing anion present in the catholyte, respectively.

Although applicable to both small-volume and large-volume samples, the methods are particularly well suited for small-volume samples. Moreover, when applied to capillary electrophoresis, the methods described herein permit desalting of a sample in the same capillary tube as is used for the electrophoretic analysis. Alternatively, however, the sample can be withdrawn from the capillary tube following desalting and processed by techniques other than high-performance capillary electrophoresis (HPCE). Regardless of which method is used, the on-tube desalting techniques described herein are rapid, highly reproducible, and they give a high recovery compared to dialysis.

The invention extends to a wide range of embodiments, the features and advantages of which will be apparent from the detailed description which follows.

BRIEF DESCRIPTION OF THE DRAWINGS

The eight subparts to FIG. 1 attached hereto are strip-chart recorder traces from an ultraviolet absorption detector, representing the isoelectric focusing of an IEF protein standard mixture.

DETAILED DESCRIPTION OF THE INVENTION AND PREFERRED EMBODIMENTS

Figure 1C:
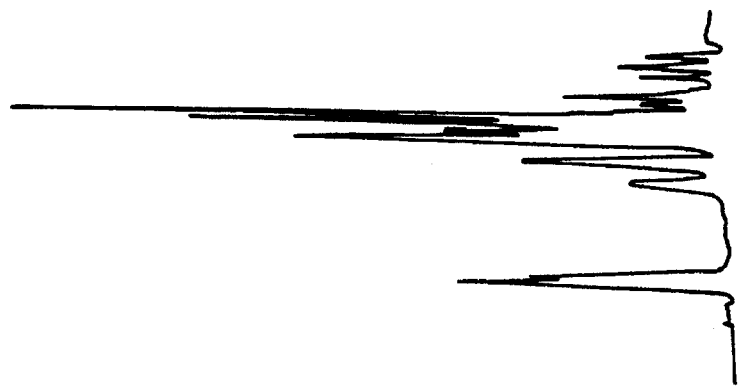
FIG. 1. Isoelectric focusing of IEF protein standard mixture both with and without desalting. Replacement of salt with ampholytes was performed at 30 μA constant current, and completed when the voltage reached 3,000 V. 3% Bio-Lyte® pH 3/10 titrated to pH 4.0 and 11.0 served as anolyte and catholyte, respectively. Isoelectric focusing, without desalting, of an IEF protein standard mixture containing no NaCl (FIG. 1A); Isoelectric focusing, without desalting, of an IEF protein standard mixture having a NaCl concentration of 0.010 mol/mL (FIG. 1B); Isoelectric focusing, without desalting, of an IEF protein standard mixture having a NaCl concentration of 0.025 mol/L (FIG. 1C); Isoelectric focusing, without desalting, of an IEF protein standard mixture having a NaCl concentration of 0.050 mol/L (FIG. 1D); Isoelectric focusing, with desalting, of an IEF protein standard mixture having a NaCl concentration of 0.100 mol/L (FIG. 1E); Isoelectric focusing, with desalting, of an IEF protein standard mixture having a NaCl concentration of 0.100 mol/L (FIG. 1F); Isoelectric focusing, with desalting, of an IEF protein standard mixture having a NaCl concentration of 0.300 mol/L (FIG. 1G); and Isoelectric focusing, with desalting, of an IEF protein standard mixture having a NaCl concentration of 0.500 mol/L (FIG. 1H). See, Table I, infra.

In one aspect of the present invention, a method is provided for the desalting of a solute sample, the method comprising: (a) mixing the solute sample with an ampholytic separation medium to form a mixture, the ampholytic separation medium containing components capable of forming a pH gradient during isoelectric focusing, said pH gradient covering the isoelectric point(s) of the solute(s) present in the solute sample; (b) filling a capillary tube with the mixture, the capillary tube having a first end in contact with an anolyte and a second end in contact with a catholyte, the anolyte and the catholyte being ampholytic media, the anolyte differing in pH from the catholyte by a pH differential; and (c) applying a voltage between the anolyte and the catholyte of sufficient intensity to cause the salt present in the solute sample to be replaced by the ampholytes present in the ampholytic media of the anolyte and the catholyte.

The desalting methods of the present invention can be used to desalt solute samples of ionic polymers or weak electrolytes, preferably ampholytes (e.g., peptides, proteins and glycoconjugates) or, compounds which can be transformed into these classes of substances by complex formation. Salts which can be removed from the forgoing samples include, but are not limited to, the following: chlorides, bromides, nitrates, carbonates, aluminates, sulphates, silicates, phosphates, etc. As such, the methods of the present invention can be used to remove the following ions (and, in turn, their counterions) from the biological sample of interest: $Na^+$, $K^+$, $Ca^{++}$, $Mg^{++}$, $NH_4^+$, $Cl^-$, $Br^-$, $F^-$, $CO_3^{2-}$, $PO_4^-$, etc.

Prior to filling the capillary tube with the sample to be desalted, the sample is mixed or diluted with an ampholyte, i.e., a mixture of species having a pH range and which is included for the purpose of forming a pH gradient. The ampholyte is generally present at a concentration ranging from about ½% to about 6% and, more typically, from about 1% to about 3%. The ampholyte that is used as the separation medium is referred to herein as the "ampholytic separation medium" or "ampholytic media" to distinguish it from the ampholyte in the sample to be desalted. In selecting an appropriate separation medium to be used in the methods of the present invention, it is important to note that the ampholytic separation medium must contain components capable of forming a pH gradient during isoelectric focusing, the pH gradient covering the isoelectric points of all of the solutes present in the sample to be desalted.

In accordance with the methods of the present invention, the ampholytic separation media may include liquids, gels and suspensions. Liquid ampholytic separation media are generally preferred. Examples of suitable ampholytic separation media include, but are not limited to, the following: BIOLYTE®, a series of ampholytes characterized by different pH ranges, available from Bio-Rad Laboratories, Inc. (Hercules, Calif., U.S.A.); PHARMALYTE ampholytes, a similar series of carrier ampholytes characterized by different pH ranges, available from Pharmacia Biotech (Uppsala, Sweden); SERVALYTES®, a similar series of carrier ampholytes characterized by different pH ranges available from Serva Chemical Co. (Heidelberg, Germany); BUFFALYTE®, a similar series of carrier ampholytes characterized by different pH ranges, available from Pierce Chemical Co. (Rockford, Ill., U.S.A.); and AMPHOLINES, a similar series formerly available from LKB (Bromma, Sweden), and currently available from Pharmacia Biotech (Uppsala, Sweden). In addition to the foregoing commercially available ampholytic separation media, one of ordinary skill in the art can synthesize synthetic ampholytes. For a review of the synthesis of synthetic ampholytes, see, e.g., O. Vesterberg, *Acta. Chem. Scand*, 23:2653 (1969), the teachings of which are hereby incorporated by reference.

In this method of the present invention, the capillary tube used for the desalting of the sample has a first end in contact with an anolyte and a second end in contact with a catholyte. The anolyte and the catholyte are ampholytic media, and the anolyte differs in pH from the catholyte by a pH differential. As previously explained, suitable ampholytic media include, but are not limited to, the following: BIO-lyte®, a series of carrier ampholytes characterized by different pH ranges; PHARMALYTE®, a series of carrier ampholytes characterized by different pH ranges; SERVALYTE®, a series of carrier ampholytes characterized by different pH ranges; BUFFALYTE®, a series of carrier ampholytes characterized by different pH ranges; BUFFALYTE®, a series of carrier ampholytes characterized by different pH ranges. It should be noted that the particular ampholytic media used as the anolyte and the catholyte can be the same or different as that used for the ampholytic separation medium, provided the pH ranges of the ampholytes employed are roughly the same. Preferably, the ampholytic media used as the anolyte and the catholyte is the same as that used for the ampholytic separation medium, e.g., BIO-LYTE® (pH 3/10), a series of carrier ampholytes having a working pH range from about 3 to about 10 is used for both the ampholytic media and the ampholytic separation medium. In this instance, it will be readily apparent to those in the art that the ampholytic media is titrated to the desired pH with, for example, hydrochloric acid and used as the anolyte. Similarly, the ampholytic media, the same as that used as the anolyte, is titrated to the desired pH with, for example, sodium hydroxide and used as the catholyte.

In this particular method, the anolyte has a pH lower than the pI of the most acidic ampholyte present in the ampholytic separation medium, and the catholyte has a pH higher than the pI of the most basic ampholyte present in the ampholytic separation medium. For instance, if the most acidic ampholyte has a pI of about 4.0, the pH of the anolyte could be, for example, 3.0. Moreover, if the most basic ampholyte has a pI of about 9.6, the pH of the catholyte could be, for example, 10.0. By selecting the pH of the anolyte and the catholyte in this manner, the ampholytes present in both the sample and the ampholytic separation medium will be prevented from migrating into the anolyte and/or the catholyte. If, however, an ampholyte happened to enter the anolyte, for example, it would be positively charged and return to the capillary tube. Again, it is important to note that the ampholytic separation medium should have a pH gradient covering the isoelectric points of all of the solutes present in the sample to be desalted.

To exchange the salt present in the solute sample with the ampholytes present in ampholytic media of the anolyte and the catholyte, a voltage is applied between the anolyte and the catholyte of sufficient intensity to cause the salt present in the solute sample to be replaced by the ampholytes present in the ampholytic media of the anolyte and the catholyte. It should be noted that the voltage is applied between the anolyte and the catholyte until the conductivity of the mixture in the capillary tube, i.e., the sample in the ampholytic separation medium, is about equal to the conductivity of the ampholytic separation medium in the absence of salt. The conductivity of the mixture in the capillary tube and the conductivity of the ampholytic separation medium in the absence of salt can readily be determined using standard methods and conventional techniques known to and used by those of ordinary skill in the art.

In another aspect of the present invention, a method is provided for the desalting of a sample in an ampholytic separation medium having a first end in contact with an anolyte and a second end in contact with a catholyte differing in pH from the anolyte by a pH differential, the method comprising: (a) introducing a displacing cation into the anolyte and a displacing anion into the catholyte, the displacing cation having a mobility less than the mobility of the cation to be removed from the sample, the displacing anion having a mobility less than the mobility of the anion to be removed from the sample; and (b) applying a voltage between the anolyte and the catholyte of sufficient intensity to cause the cation and the anion to be removed from the sample to be replaced by the displacing cation present in the anolyte and the displacing anion present in the catholyte, respectively.

As with the previously described method, the sample (i.e., ionic polymers or weak electrolytes, preferably ampholytes, e.g., peptides, proteins and nucleic acids) to be desalted is mixed or diluted with an ampholytic separation medium having a first end in contact with an anolyte and a second end in contact with a catholyte differing in pH from the anolyte by a pH differential. Suitable ampholytic separation media include, but are not limited to, the following: BIOLYTE®, a series of carrier ampholytes characterized by different pH ranges, PHARMALYTE®, a series of carrier ampholytes characterized by different pH ranges; SERVALYTE®, a series of carrier ampholytes characterized by different pH ranges; BUFFALYTE®, a series of carrier ampholytes characterized by different pH ranges; BUFFALYTE®, a series of carrier ampholytes characterized by different pH ranges. Alternatively, synthetic ampholytes can be produced in accordance with the methods described by Vesterberg, supra (1969). As with the previously described method, the ampholytic separation medium should be selected so that it has a pH range coveting the isoelectric points of all of the solutes present in the sample.

In this method of the present invention, a displacing cation is introduced into the anolyte and a displacing anion is introduced into the catholyte. To be effective, the displacing cation must have a mobility less than the mobility of the cation to be removed from the sample, and the displacing anion must have a mobility less than the mobility of the anion to be removed from the sample. Cations and anions which can be removed from a sample using this method of the present invention include, but are not limited to, the cations and anions resulting from the dissociation of chlorides, bromides, nitrates, carbonates, aluminates, sulphates, silicates, phosphates, etc., in water. Moreover, ions which can be removed from a sample using this method of the present invention include those ions whose presence in the sample causes the pH gradient of the ampholytic separation medium to be narrowed, and whose absence (i.e., removal) from the sample results in the sample (i.e., the sample in the ampholytic separation medium) having a conductivity equivalent to the conductivity of the ampholytic separation medium in the absence of salt.

In a presently preferred embodiment, the displacing cation has a mobility about five-fold to about ten-fold less than the mobility of the cation to be removed, while the displacing anion has a mobility about five-fold to about ten-fold less than the mobility of the anion to be removed. It should be noted that the mobilities of the ions to be removed from the sample and, in turn, the displacing cations and anions can be measured using standard techniques known to those of skill in the art. In addition to having mobilities less than the ions to be removed, the displacing cations and anions used should be high in molecular weight. In addition, the displacing cations should have a pK of about 11, and the displacing anions should have a pK of about 3. Suitable ions cations include, for example, amino acids.

As with the previously described method, to effect removal of the ions of interest, a voltage is applied between the anolyte and the catholyte of sufficient intensity to cause the cation(s) and the anion(s) that are to be removed from the sample to be replaced by the displacing cation present in the anolyte and the displacing anion present in the catholyte, respectively. It should be noted that the voltage is applied between the anolyte and the catholyte until the conductivity of the mixture (i.e., the sample in the ampholytic separation medium) in the capillary tube is about equal to the conductivity of the ampholytic separation medium in the absence of salt.

The capillary tubes used in the methods of the present invention are conventional capillary tubes. The size of the capillary tube in terms of both length and internal diameter is not critical to the invention. Thin-walled, thin diameter tubes are preferred. Typically, the capillary tube has an internal diameter ranging from about 25 microns to about 500 microns. Also preferred are fused silica capillaries. The inner walls of the capillary tube may be treated with a monolayer of a polymer, examples of which include linear polyacrylamide, dextran and methyl cellulose, to eliminate zone distortion due to electroendosmosis and the adsorption of solutes by the capillary tube wall. The treatment agent may be deposited by conventional methods well known in the art of manufacturing capillaries.

For electrophoretic desalting and separation, the voltage used is not critical to the invention, and may vary widely. Typical voltages range from about 500 V to about 30,000 V, preferably from about 1,000 V to about 10,000 V.

It should be noted that when applied to capillary electrophoresis, the methods described herein permit desalting of a sample in the same capillary tube as is used for the electrophoretic analysis. Alternatively, however, the sample can be withdrawn from the capillary tube following desalting and processed by techniques other than high-performance capillary electrophoresis (HPCE).

The foregoing desalting methods can best be understood by taking into account the theoretical considerations upon which such methods are founded. In understanding the theory behind the methods of the present invention, one of ordinary skill in the art will be able to make modifications and variations in the materials and/or procedures described herein without departing from the spirit and scope of the invention.

To understand more fully the theory behind the methods of the present invention, consider, for example, the boundary between the anolyte and the ampholytic separation medium in the capillary tube during a focusing step. The number of protons, $N_{H^+}$, passing electrophoretically from the anolyte to the boundary per time unit can be expressed by the following equation:

$$N_{H+} = \frac{I u_H + n_{H+}}{\kappa} \quad (1)$$

wherein I=the current, $u_{H^+}$=the mobility of the protons in the anolyte, $n_{H^+}$=the number of protons per volume unit, and κ=the conductivity in the anolyte (Hjertén, et al., *J. Chromatogr.*, 387:127–138 (1987)). It has been found that ampholytic media containing ampholytes diluted in water have a high ohmic resistance which further increases during focusing when the voltage is applied. Due to the low current, the amount of protons entering the capillary is limited according to Equation 1 and, thus, the pH gradient of the ampholytic separation medium is not affected.

In the presence of a sample containing salt (e.g., 0.1M NaCl), the number of protons, $N_{H^+}$, passing electrophoretically from the anolyte to the boundary per time unit can be similarly expressed by the following equation:

$$N'_{H+} = \frac{I' u'_{H+} n'_{H+}}{\kappa'} \quad (2)$$

wherein I'=the current in the tube in the presence of salt, $u'_{H^+}=u_{H^+}$, $n'_{H^+}=n_{H^+}$ and κ'=κ. It has been found, however, that in a 0.1M NaCl sample solution, the current, I', is about 20 times greater than the current when NaCl is absent. Combining Equations 1 and 2, the following equation is obtained:

$$\frac{N_{H+}}{N'_{H+}} = \frac{I}{I'} \quad (3)$$

Based on the combination of Equations 1 and 2, the number of protons, $N_{H+}$, passing electrophoretically from the anolyte to the boundary per time unit increases 20-fold, i.e., $N'_{H^+}=20\ N_{H^+}$.

As such, in the presence of a sample containing salt, the number of protons entering the capillary tube from the anolyte increases about 20 fold and then gradually decreases until most of the $Na^+$ ions move out electrophoretically out of the capillary tube. This decrease in pH at the anodic section causes the ampholytes to become positively charged and, in turn, to migrate toward the cathode. A similar situation occurs at the cathode, where a large amount of $OH^-$ ions enter the capillary tube giving rise to a pH increase that forces the ampholytes to migrate toward the anode. As a result, the focused zones are confined to a distance of 3–4 cm in the central part of the capillary, where a large degree of heat is generated thereby increasing the risk of protein precipitation (Zhu, et al., *J. Chromatogr.*, 559:479–488 (1991)). As expected, it has been found that the length of the pH gradient decreases with increasing amounts of salt in the sample (See, Table 1, infra).

Using the method of the present invention, however, the salt present in the solute sample can be replaced by the ampholytes present in the ampholytic media of the anolyte and the catholyte. Again, in this method, the anolyte is an ampholytic medium having a pH lower than the pI of the most acidic ampholyte present in said ampholytic separation medium, while the catholyte is an ampholytic medium having a pH higher than the pI of the most basic ampholyte present in said ampholytic separation medium. Under these conditions, Equation 1 now takes the form:

$$N''_{H+} = \frac{I'' u''_{H+} n''_{H+}}{\kappa''} \quad (4)$$

where κ''=2κ' (found experimentally) and $n''_{H^+}$=1/200 n' + (0.0001/0.02), I''=I'. Accordingly, $N''_{H^+}$=1/400 $N'_{H^+}$. Similarly, at the cathodic end $N''_{OH^-}$=1/400 $N'_{OH^-}$. Therefore, the amount of $H^+$ at the anodic end and $OH^-$ at the cathodic end during the removal of salt decreases about 400 fold when the sample contains 0.1M NaCl. In addition, the concentrations of $H^+$ and $OH^-$ decrease further along the capillary as they meet and react with the buffering ampholytes passing electrophoretically from the electrode vessels into the capillary tube. Moreover, the mobility of the ampholytes is much lower than that of $Na^+$ and, thus, the current will decrease as the $Na^+$ ions are replaced by ampholytes moving into the capillary tube. Replacement of the salt present in the solute sample is complete when the conductivity of the mixture in the capillary tube is about equal to the conductivity of the ampholytic separation medium in the absence of salt.

In addition to the foregoing, it has also been discovered that the desalting of biological samples can be accomplished not only by ampholytes, but also by ions, i.e., displacing anions and cations, of low mobility. From Equation 1, it is recognized that a decrease in, for example, $N_{H^+}$ can be achieved by a reduction in current (I), which is governed by the following equation:

$$I = \frac{V}{R} \quad (5)$$

and $$R = \frac{l}{q\kappa} \quad (6)$$

wherein l =the length of capillary and q=its cross-sectional area. Combining Equations 5 and 6, the following relationship is obtained:

$$I = \frac{Vq\kappa}{l} \quad (7)$$

The conductivity, κ, is determined by the following equation:

$$\kappa = \frac{F}{1000} \times \Sigma C_i \times u_i \quad (8)$$

wherein F=the Faraday constant and C=the concentration in gram equivalents per liter of solution. As such, displacing cations and anions (with pK≧11 and ≦3, respectively) that have high molecular weights and low mobilities, can be used instead of ampholytes in the electrode vessel for the desalting of biological samples.

Moreover, due to the low ampholyte concentration in the sample solution (below 0.01M) and neglecting the influence from $H^+$ and $OH^-$, the Kohlrausch regulating function, $\omega$, for the phases separated by the moving boundary between $Na^+$ and the displacing ion $X^+$ (migrating into the capillary tube from the anolyte) can be expressed by the following equation:

$$\omega^\alpha = \frac{C^\alpha_{Na+}}{U^\alpha_{Na+}} + \frac{C^\alpha_{Cl-}}{U^\alpha_{Cl-}} \qquad (9)$$

and $$\omega^\beta = \frac{C^\beta_{x+}}{U^\beta_{x+}} + \frac{C^\beta_{Cl-}}{U^\beta_{Cl-}} \qquad (10)$$

respectively (S. Hjertén, *Topics in Bioelectrochemistry and Bioenergetics*, (G. Milazzo (ed.)), Vol. 2, 103–106 (1978), the teachings of which are hereby incorporated by reference). Since $\omega^\alpha = \omega^\beta$, $$\frac{C^\alpha_{Na+}}{U^\alpha_{Na+}} + \frac{C^\alpha_{Cl-}}{U^\alpha_{Cl-}} = \frac{C^\beta_{x+}}{U^\beta_{x+}} + \frac{C^\beta_{Cl-}}{U^\beta_{Cl-}} \qquad (11)$$

Utilizing the conditions for electroneutrality and putting $C^\alpha_{Na+} \approx C^\alpha_{Cl-}$, $C^\beta_{x+} = C^\beta_{Cl-}$, $U^\alpha_{Cl-} = U^\beta_{Cl-} \approx U^\alpha_{Na+}$, the following equation is obtained:

$$C^\beta_{x+} = \frac{2 \times C^\alpha_{Na+} \times U^\beta_{x+}}{U^\alpha_{Na+} + U^\beta_{x+}} \qquad (12)$$

Therefore, if the displacing ion has, for example, one-tenth of the mobility of the $Na^+$, the concentration of this ion will be 2/11 of $Na^+$ concentration ($U_{x+} = 1/10\ U_{Na+}$, $C_{x+} = 2/11\ C_{Na+}$). As such, the conductivity ($\kappa_2$) in the capillary following removal of the salt in the sample is expressed by the following equation:

$$\kappa_2 = \frac{F}{1000} \left( \frac{2}{11} \times C_{Na+} \times \frac{1}{10} \times U_{Na+} + \frac{2}{11} \times C_{Cl-} \times \frac{1}{10} \times U_{Cl-} \right) \qquad (13)$$

Similarly, the conductivity ($\kappa_1$) prior to removal of the salt in the sample is expressed by the following equation:

$$\kappa_1 = \frac{F}{1000} (C_{Na+} \times U_{Na+} + C_{Cl-} \times U_{Cl-}) \qquad (14)$$

Consequently, $\kappa_2/\kappa_1 = 2/110$. As such, contribution from the displacing ion to the current will also be reduced as can be seen by Equation 7. Due to this lower current, there will be a reduction in the number of $H^+$ and $OH^-$ to the extent that the pH gradient will remain unaffected. One of the advantages of using the displacing anion and cation instead of the ampholyte solution is that the pIs of the displacing anion and cation can be selected to be outside the pH range of the ampholyte gradient. In this instance, the displacing ion will be removed during isoelectric focusing. Alternatively, it may be advantageous to have the pIs of the displacing anion and cation be within the pH range of the ampholyte gradient if their ultimate locations inside the gradient would either aid in the separation or, not disturb it.

Regardless of which method is used, the on-tube desalting techniques described herein are rapid, highly reproducible, and they give a high recovery compared to dialysis.

The following examples are offered for illustrative purposes only, and are intended neither to define or limit the invention in any manner.

EXAMPLE I

This example illustrates isoelectric focusing of IEF protein standard mixture with and without the use of the desalting methods of the present invention.

A. Materials and Equipment

An IEF protein standard mixture and Bio-Lyte® (pH 3/10), a series of carrier ampholytes characterized by pH gradient ranging from about pH 3 to pH 10, were obtained from Bio-Rad Laboratories, Inc. (Richmond, Calif., U.S.A.). The IEF protein standard mixture contained the following proteins:

Phycocyanin (pI=4.65);
β-Lactoglobulin B (pI=5.10);
Bovine carbonic anhydrase (pI=6.00);
Human carbonic anhydrase (pI=6.50);
Equine myoglobin (pI=7.00);
Human hemoglobin A (pI=7.0);
Human hemoglobin C (pI=7.10);
Lentil lectin (three bands) (pIs=7.8, 8.0 and 8.2); and
Cytochrome C (pI=9.6).

The separations capillary, made from fused silica and obtained from Polymicro Technologies (Phoenix, Ariz., U.S.A.), had a length of 150 mm and an inside diameter of 0.1 mm with a wall thickness of 0.1 mm. The on-tube detector was a modified Spectroflow 783 from ABI Analytical Kratos Division (Ramsey, N.J., U.S.A.). The detection point was 15 mm from the cathodic end of the capillary.

B. Replacement Of Salt With Ampholytes

The capillary was coated internally with linear polyacrylamide covalently attached to the wall using the method of Hjertén (*J. Chromatogr.*, 347:191–198 (1985)). The IEF protein standard mixture was diluted 1:20 in 1.5% Bio-Lyte® pH 3/10, and to this solution varying amounts of solid sodium chloride was added (See, Table 1). The coated capillaries were filled with the various solutions. 3% Bio-Lyte® pH 3/10 was titrated to pH 4.0 by 2.0M hydrochloric acid and served as anolyte. In addition, 3% Bio-Lyte® was titrated to pH 11.0 by 2.0M sodium hydroxide and used as catholyte. Electrophoretic replacement of salt with ampholytes was performed at 30 μA constant current. Replacement of the salt present in the sample is complete when the conductivity of the mixture in the capillary tube becomes close to that of a 1.5% ampholyte solution in the absence of salt, e.g., in our experiments when the voltage has increased to 3,000 V at a constant current of 30 μA. The time for replacement of salt was dependent on the salt concentration (See, Table 1).

C. Focusing And Mobilization Of Proteins

Focusing was performed at 3,000 V constant voltage for 8 min. Phosphoric acid (0.02M) served as the anolyte and 0.02M sodium hydroxide as the catholyte. The width of the pH gradient was determined by measuring the distance between the two focused proteins zones, phycocyanin (pI=4.65) and cytochrome C (pI=9.6) (See, Table 1). Cathodic mobilization was initiated by replacing the 0.02M sodium hydroxide catholyte with 0.02M phosphoric acid. mobilization was performed at constant voltage of 3,000 V. The migrating zones were monitored at 280 nm as they passed a stationary UV detector. Mobilization occurs in one direction only. Therefore, proteins which focus at a pH around 10 may not be detected by the UV monitor upon cathodic mobilization (e.g., cytochrome C in FIG. 1, A–C), since their steady state positions may be between the detector window and the cathode. However, upon desalting, cytochrome C can easily be detected (See, FIG. 1, F–H).

TABLE I

THE INFLUENCE OF DESALTING ON THE WIDTH OF THE pH GRADIENT

| | NaCl conc. in sample (mol/L) | Desalting | Width of pH gradient (cm) |
|---|---|---|---|
| A | 0 | No | 9.0 |
| B | 0.010 | No | 8.0 |
| C | 0.025 | No | 6.0 |
| D | 0.050 | No | 4.7 |
| E | 0.100 | No | 3.2 |
| F | 0.100 | Yes, 5 min | 9.3 |
| G | 0.300 | Yes, 15 min | 9.0 |
| H | 0.500 | Yes, 30 min | 8.8 |

Figure 1B:
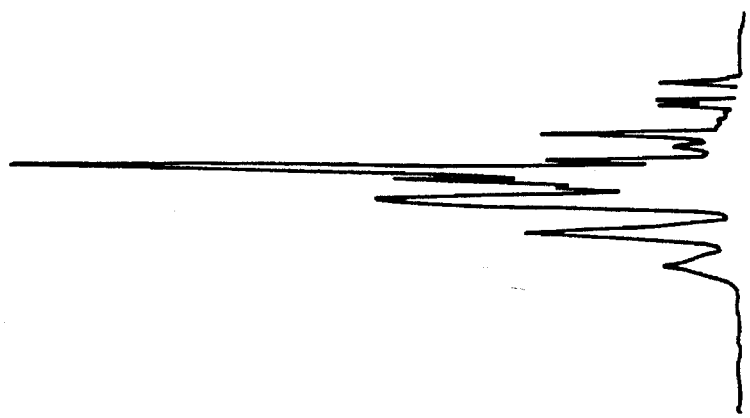
Figure 1A:
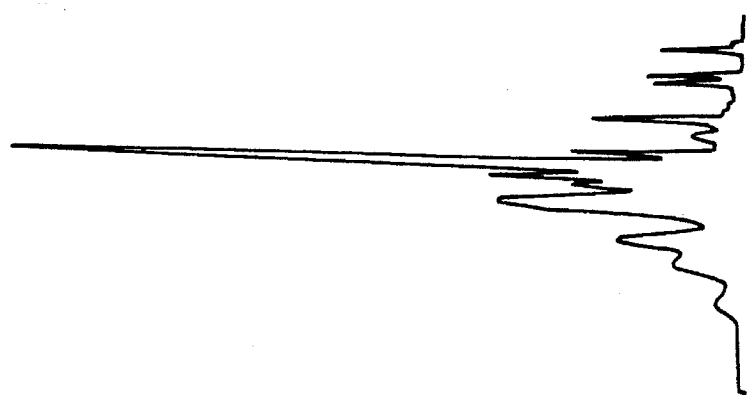

For the study of IEF without replacement of salt, the risk of overheating during focusing was avoided by using a constant current of 30 μA until the voltage reached 3,000 V, and then keeping the voltage constant for 8 minutes (See, FIG. 1, A–E).

The foregoing is offered primarily for purposes of illustration. It will be readily apparent to those skilled in the art that modifications and variations of the materials and/or procedures described herein may be introduced with successful results without departing from the spirit and scope of the invention.

The teachings of all references cited hereinabove are hereby incorporated by reference for all purposes.

What is claimed is:

1. A method for desalting a solute sample, said method comprising:
   (a) mixing said solute sample with an ampholytic separation medium to form a mixture, said ampholytic separation medium containing components that form a pH gradient during isoelectric focusing, said pH gradient covering the isoelectric point(s) of the solute(s) present in said solute sample;
   (b) filling a capillary tube with said mixture, said capillary tube having a first end in contact with an anolyte and a second end in contact with a catholyte, said anolyte and said catholyte being ampholytic media, said anolyte differing in pH from said catholyte by a pH differential; and
   (c) applying a voltage between said anolyte and said catholyte of sufficient intensity to cause the salt present in said solute sample to be replaced by ampholytes present in said ampholytic media of said anolyte and said catholyte.

2. A method in accordance with claim 1 wherein said ampholytic separation medium is a liquid solution.

3. A method in accordance with claim 1 wherein said ampholytic media of said anolyte and said catholyte are liquid solutions.

4. A method in accordance with claim 1 wherein said anolyte has a pH lower than the pI of the most acidic ampholyte present in said ampholytic separation medium, and said catholyte has a pH higher than the pI of the most basic ampholyte present in said ampholytic separation medium.

5. A method in accordance with claim 1 wherein said ampholytic separation medium has a pH gradient ranging from a pH of about 3 to a pH of about 10.

6. A method in accordance with claim 5 wherein said anolyte has a pH of about 3 to about 4 and said catholyte has a pH of about 10 to about 11.

7. A method in accordance with claim 1 wherein said ampholytic separation medium and said ampholytic media of said anolyte and said catholyte are the same.

8. A method in accordance with claim 1 wherein said voltage is applied between said anolyte and said catholyte until the conductivity of said mixture in said capillary tube is about equal to the conductivity of said ampholytic separation medium in the absence of salt.

9. A method in accordance with claim 8 wherein said capillary tube is coated with a monolayer of a polymer prior to filling said capillary tube with said mixture.

10. A method in accordance with claim 9 wherein said polymer is a member selected from the group consisting of polyacrylamide, dextran and methyl cellulose.

11. A method in accordance with claim 1 wherein said capillary tube has an internal diameter ranging from about 25 microns to about 500 microns.

12. A method for desalting a sample in an ampholytic separation medium having a first end in contact with an anolyte and a second end in contact with a catholyte differing in pH from said anolyte by a pH differential, said method comprising:
   (a) introducing a displacing cation into said anolyte and a displacing anion into said catholyte, said displacing cation having a mobility less than the mobility of the cation to be removed from said sample, said displacing anion having a mobility less than the mobility of the anion to be removed from said sample; and
   b) applying a voltage between said anolyte and said catholyte of sufficient intensity to cause the cation and the anion to be removed from said sample to be replaced by said displacing cation present in said anolyte and said displacing anion present in said catholyte, respectively.

13. A method in accordance with claim 12 wherein said displacing cation has a mobility about five-fold to about ten-fold less than the mobility of the cation to be removed from said sample.

14. A method in accordance with claim 12 wherein said displacing anion has a mobility about five-fold to about ten-fold less than the mobility of the anion to be removed from said sample.

15. A method in accordance with claim 12 wherein said displacing cation has a mobility about five-fold less than the mobility of the cation to be removed from said sample, and said displacing anion has a mobility about five-fold less than the mobility of the anion to be removed from said sample.

16. A method in accordance with claim 12 wherein said displacing cation has a mobility about ten-fold less than the mobility of the cation to be removed from said sample, and said displacing anion has a mobility about ten-fold less than the mobility of the anion to be removed from said sample.

17. A method in accordance with claim 12 wherein said displacing cation has a pK of about 11 and said displacing anion has a pK of about 3.

18. A method in accordance with claim 12 wherein said voltage is applied between said anolyte and said catholyte until the conductivity of said sample in said ampholytic separation medium is about equal to the conductivity of said ampholytic separation medium in the absence of salt.

19. A method in accordance with claim 12 wherein said ampholytic separation medium is a liquid solution in a capillary having an internal diameter of 500 microns or less.

20. A method in accordance with claim 12 wherein said ampholytic separation medium is a liquid solution in a capillary having an internal diameter of 100 microns or less.

* * * * *